United States Patent [19]

Alabaster et al.

[11] Patent Number: 5,668,280

[45] Date of Patent: Sep. 16, 1997

[54] CHEMICAL SYNTHESIS OF A CHIRAL OXAZINONE

[75] Inventors: Ramon John Alabaster, Puckeridge; Ian Frank Cottrell, Hertford; Andrew William Gibson, Welwyn Garden City; Simon Adrian Johnson, Bishops Stortford, all of England

[73] Assignee: Merck Sharp & Dohme Limited, Hoddessdon, England

[21] Appl. No.: 652,081

[22] Filed: May 23, 1996

[30] Foreign Application Priority Data

Jun. 1, 1995 [GB] United Kingdom ............... 9511031

[51] Int. Cl.$^6$ ................................. C07D 265/32
[52] U.S. Cl. ................................. 544/173
[58] Field of Search ................................. 544/173

[56] References Cited

FOREIGN PATENT DOCUMENTS

| 0 577 394 | 1/1994 | European Pat. Off. |
| WO95/16679 | 6/1995 | WIPO |

OTHER PUBLICATIONS

D.A. Evans, et al., *J. Am. Chem. Soc.*, (1990) 112, 4011–4030.

*Primary Examiner*—Mukund J. Shah
*Assistant Examiner*—Bruck Kifle
*Attorney, Agent, or Firm*—J. Eric Thies; David L. Rose

[57] ABSTRACT

The present invention provides a process for the preparation of substantially pure N-benzyl-3-(S)-(4-fluorophenyl)-1,4-oxazin-2-one which comprises:

(i) contacting racemic N-benzyl-3-(4-fluorophenyl)-1,4-oxazin-2-one with (−)-3-bromocamphor-8-sulphonic acid (hereinafter referred to as (−)-3-BCS) in the presence of a racemising agent;

(ii) collecting the resultant crystalline (−)-3-BCS salt of N-benzyl-3-(S)-(4-fluorophenyl)-1,4-oxazin-2-one; and (iii) liberating the free base of N-benzyl-3-(S)-(4-fluorophenyl)-1,4-oxazin-2-one by treatment of the (−)-3-BCS salt collected in step (ii) with aqueous base.

11 Claims, No Drawings

CHEMICAL SYNTHESIS OF A CHIRAL OXAZINONE

The present invention relates to a process for the preparation of a chiral 1,4-oxazin-2-one derivative which is useful as an intermediate in the preparation of certain therapeutic agents. In particular, the present invention provides a process for the preparation of optically pure N-benzyl-3-(S)-(4-fluorophenyl)-1,4-oxazin-2-one which is an intermediate in the preparation of pharmaceutical compounds which are substance P (or neurokinin-1) receptor antagonists.

European patent specification No. 0 577 394-A (published 5th Jan. 1994) describes the preparation of 3-(S)-(4-fluorophenyl)-4-benzyl-2-morpholinone (hereinafter referred to as N-benzyl-3-(S)-(4-fluorophenyl)-1,4-oxazin-2-one, which has the structure:

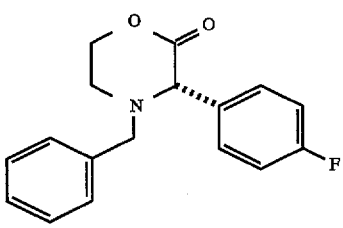

by a two-step process starting from optically pure (S)-(4-fluorophenyl) glycine. Control of process parameters (e.g. reaction time, temperature, moisture content) is necessary to prevent racemisation in these steps. With reference to Example 59 in EP-0 577 394-A, the 1,4-oxazin-2-one is prepared as follows:

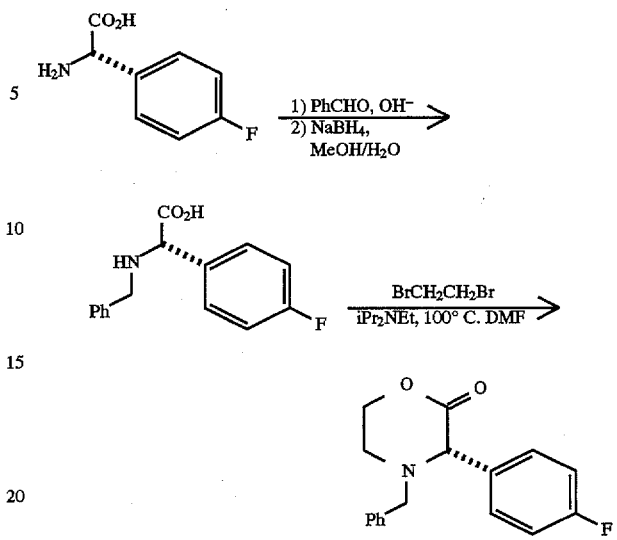

Furthermore, the preparation of optically pure (S)-(4-fluorophenyl)glycine is described in EP-0 577 394-A by means of a four-step asymmetric synthesis process which is not amenable to reproduction on a production scale. In particular, Example 58 in EP-0 577 394-A describes the following synthesis:

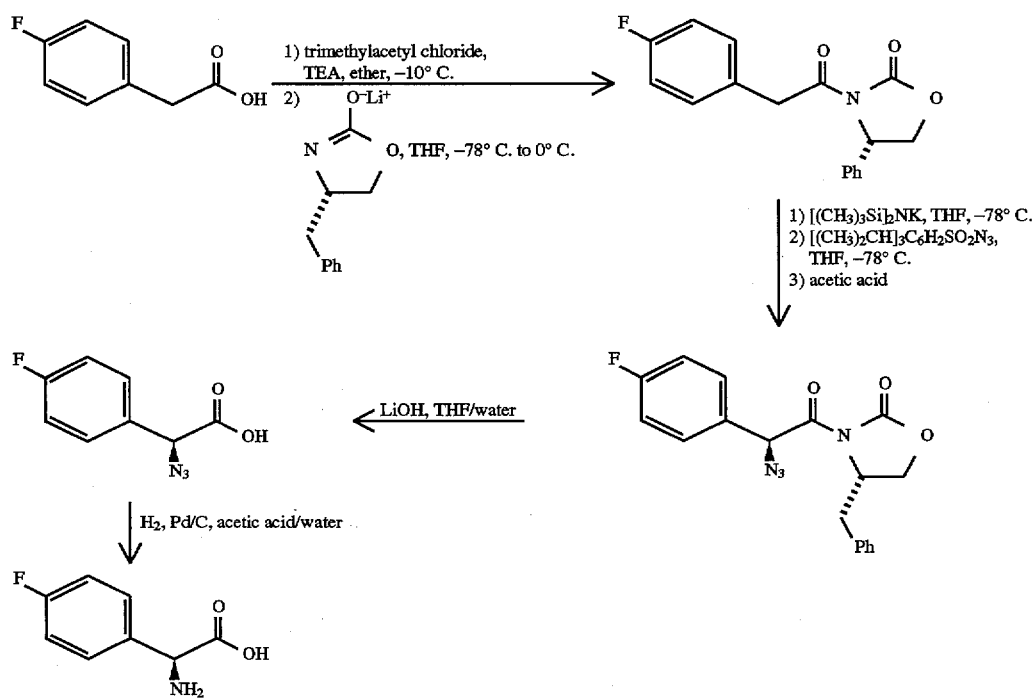

which is based upon the procedure for the asymmetric synthesis of α-amino acids described by D. A. Evans et al., *J. Am. Chem. Soc.*, (1990) 112, 4011–4030.

The complexity of this four-step process combined with the sensitive nature of the protection and double alkylation reactions to give the desired 1,4-oxazin-2-one, renders these prior art syntheses impracticable when attempted on anything other than a laboratory scale. It will be appreciated that N-benzyl-3-(S)-(4-fluorophenyl)-1,4-oxazin-2-one is an important intermediate for a particularly useful class of therapeutic agents. As such, there is a need for the development of a process which is readily amenable to scale-up and hence capable of practical application to the manufacturing plant.

The present invention accordingly provides a convenient, efficient process which utilizes racemic N-benzyl-3-(4-fluorophenyl)-1,4-oxazin-2-one as starting material and in a minimum of steps affords product of high enantiomeric purity in high yield. In a further aspect of the present invention, the undesired enantiomer is racemised in situ and recycled through the resolution process resulting in increased yield of the desired enantiomer. A further advantage of the present invention is that the desired product is obtained directly in high optical purity and yield without need for an upgrading recrystallisation.

Thus, in a first aspect of the present invention, there is provided a process for the preparation of substantially pure N-benzyl-3-(S)-(4-fluorophenyl)-1,4-oxazin-2-one which comprises:

(i) contacting racemic N-benzyl-3-(4-fluorophenyl)-1,4-oxazin-2-one with (−)-3-bromocamphor-8-sulphonic acid (hereinafter referred to as (−)-3-BCS) in the presence of a racemising agent;

(ii) collecting the resultant crystalline (−)-3-BCS salt of N-benzyl-3-(S)-(4-fluorophenyl)-1,4-oxazin-2-one; and (iii) liberating the free base of N-benzyl-3-(S)-(4-fluorophenyl)-1,4-oxazin-2-one by treatment of the (−)-3-BCS salt collected in step (ii) with aqueous base.

The undesired enantiomer remains in solution, where action of the racemising agent results in racemisation to generate more of the desired enantiomer which then crystallises as the (−)-3-BCS salt.

It will be appreciated that following removal of the (−)-3-BCS salt, the crystallisation liquors which contain the undesired enantiomer may be re-worked by the addition, if necessary, of further racemising agent and further (−)-3-BCS thereby increasing the overall yield of the desired enantiomer via the formation of further N-benzyl-3-(S)-(4-fluorophenyl)-1,4-oxazin-2-one (−)-3-BCS salt.

Suitable racemising agents of use in the present invention include organic acids such as trifluoroacetic acid or acetic acid, or mineral acids such as hydrochloric acid. Also suitable as a racemising agent is 3-bromocamphor-8-sulphonic acid.

The resolution of racemic N-benzyl-3-(4-fluorophenyl)-1,4-oxazin-2-one with (−)-3-BCS is conveniently effected in a suitable organic solvent, for example, isopropyl acetate or ethyl acetate at a temperature between 0° C. and the boiling point of the solvent, conveniently between room temperature and 100° C., for example, at about 65° C. to 90° C.

Racemisation of the undesired enantiomer may be effected at a temperature between room temperature and the boiling point of the solvent, preferably between 50° C. and 100° C., for example, at about 65° C. to 90° C. Under these conditions resolution continues to take place. The racemisation/resolution is preferably effected over 1 to 9 days, in particular over 1 to 7 days, and preferably over 3 to 6 days.

It will be appreciated that (−)-3-bromocamphor-8-sulphonic acid may conveniently be used to effect both the racemisation and the resolution of racemic N-benzyl-3-(4-fluorophenyl)-1,4-oxazin-2-one. A particularly preferred solvent for use when (−)-3-BCS is used to effect racemisation and resolution is isopropyl acetate.

Where the crystsllization liquors are re-worked as described above, additional quantities of the desired chiral oxazinone may be recovered as often as practicable, preferably at least once or twice.

Liberation of the chiral oxazinone free base from the (−)-3-BCS salt is effected using aqueous base, for example, 0.88 ammonia solution or a suitable alkali metal carbonate or hydroxide, such as potassium carbonate, sodium bicarbonate or sodium hydroxide. The free base is conveniently extracted from the (−)-3-BCS using a suitable organic solvent, for example, isopropyl acetate, ethyl acetate or dichloromethane. It will be appreciated that following collection of the liberated free base, the (−)-BCS may also be recovered and recycled using conventional procedures.

When isolating the N-benzyl-3-(S)-(4-fluorophenyl)-1,4-oxazin-2-one (−)-3-BCS salt, it will be appreciated that in order to optimise yield, the reaction mixture should be aged at reduced temperature, for example, at about 0° to 5° C., for at least 1 hour prior to collection of the (−)-3-BCS salt.

The (−)-3-BCS salt is a novel compound, thus, in a further or alternative aspect of the present invention, there is provided the compound N-benzyl-3-(S)-(4-fluorophenyl)-1,4-oxazin-2-one in the form of its 3-bromocamphor-8-sulphonic acid salt.

The following non-limiting example illustrates a process according to the present invention:

EXAMPLE 1

Racemisation/Resolution of N-benzyl-3-(4-fluorophenyl)-1,4-oxazin-2-one

To a solution of N-benzyl-4-fluorophenyl-1,4-oxazin-2-one (10 g) in isopropyl acetate (110 ml) at room temperature was added a solution of (−)-3-bromocamphor-8-sulphonic acid ((−)-3-BCS) (12 g) in acetonitrile (24 ml). Crystallisation began after 2–3 minutes. The slurry was stirred for 1 hour at room temperature. Trifluoroacetic acid (7 ml) was added and the mixture stirred at 65° C. for 3 days. The mixture was cooled to 0°–5° C., aged for 1 hour and the solid collected, washed with isopropyl acetate and dried in vacuo at 40° C., to give the N-benzyl-3-(S)-(4-fluorophenyl)-1,4-oxazin-2-one (−)-3-BCS salt: yield 17.24 g, ee 98.6% (S) isomer.

The chiral composition of the remaining liquors was determined as 79% (R),21% (S).

The liquors were stirred at 65° C. for 3 days, then cooled to 0°–5° C. The solid was collected, washed with isopropyl acetate and dried in vacuo to give a further batch of the N-benzyl-3-(S)-(4-fluorophenyl)-1,4-oxazin-2-one (−)-3-BCS salt: yield 0.84 g, ee 98.6% (S) isomer.

The chiral composition of the remaining liquors was determined as 64% (R), 36% (S).

The liquors were stripped in vacuo and the residue was dissolved in isopropyl acetate (20 ml) containing trifluoroacetic acid (1 ml) and stirred at 65° C. for 20 hours. The mixture was cooled to 0°–5° C. for 1 hour and the solid collected, washed with isopropyl acetate and dried in vacuo to give a further batch of the N-benzyl-3-(S)-(4-fluorophenyl)-1,4-oxazin-2-one (−)-3-BCS salt: yield 2.2 g, ee 99.2% (S) isomer.

Total weight of (−)-3-BCS salt: 20.28 g, 97% yield.

A sample (0.5 g) of the (−)-3-BCS salt was retained and the remainder converted back to free base. The salt was partitioned between isopropyl acetate (50 ml) and water (100 ml) containing 0.88 ammonia solution (3 ml). The layers were separated and the aqueous phase extracted with isopropyl acetate (25 ml). The combined organic phases were washed with water (25 ml). The organic phase was concentrated to residue and flushed with isopropyl acetate to give the N-benzyl-3-(S)-(4-fluorophenyl)-1,4-oxazin-2-one as the free base: yield 8.7 g, 93% recovery, ee 98.4% (S) isomer.

EXAMPLE 2

Racemisation/Resolution of N-benzyl-3-(4-fluorophenyl)-1,4-oxazin-2-one

A futher batch of N-benzyl-3-(S)-(4-fluorophenyl)-1,4-oxazin-2-one (−)-3-BCS salt was prepared substantially according to the method of Example 1 except that the following quantities and reaction conditions were used:

N-benzyl-3-(4-fluorophenyl)-1,4-oxazin-2-one (racemate) (4.96 g); (−)-3-BCS in acetonitrile (1.85M; 9.4 ml); trifluoroacetic acid (2.1 ml); and isopropyl acetate (55 ml). The mixture was stirred at 90° C. for 6 days and then cooled to 0°–5° C. and aged for 1 hour. The solid N-benzyl-3-(S)-(4-fluorophenyl)-1,4-oxazin-2-one (−)-3-BCS salt was collected and washed with isopropyl acetate (20 ml).

Yield 9.40 g (90%); ee 99.6% (S) isomer.

The chiral composition of the remaining liquors was determined as 88% (R), 12% (S).

EXAMPLE 3

Racemisation/Resolution of N-benzyl-3-(4-fluorophenyl)-1,4-oxazin-2-one using (−)-3-bromocamphor-8-sulphonic acid A solution of N-benzyl-4-fluorophenyl-1,4-oxazin-2-one (5 g) in isopropyl acetate (16.76 ml) was diluted with isopropyl acetate (37.6 ml) and a solution of (−)-3-bromocamphor-8-sulphonic acid ((−)-3-BCS) (5.73 g) in isopropyl acetate (20.67 ml) added at room temperature. Crystallisation began after approximately 20 minutes. The mixture was stirred for 1 hour at room temperature and then stirred at 75° C. for 9 days. The mixture was then cooled to room temperature, aged at 0°–5° C. for 1 hour and the solid collected, washed with isopropyl acetate to give the N-benzyl-3-(S)-(4-fluorophenyl)-1,4-oxazin-2-one (−)-3-BCS salt: yield 10.5 g, ee 96.5% (S) isomer.

We claim:

1. A process for the preparation of substantially pure N-benzyl-3-(S)-(4-fluorophenyl)-1,4-oxazin-2-one which comprises:
   (i) contacting racemic N-benzyl-3-(4-fluorophenyl)-1,4-oxazin-2-one with (−)-3-bromocamphor-8-sulphonic acid (hereinafter referred to as (−)-3-BCS) in the presence of a racemising agent;
   (ii) collecting the resultant crystalline (−)-3-BCS salt of N-benzyl-3-(S)-(4-fluorophenyl)-1,4-oxazin-2-one; and
   (iii) liberating the free base of N-benzyl-3-(S)-(4-fluorophenyl)-1,4-oxazin-2-one by treatment of the (−)-3-BCS salt collected in step (ii) with aqueous base.

2. A process as claimed in claim 1 wherein the crystallisation liquors remaining after step (ii) are re-worked by the addition, if necessary, of further racemising agent and further (−)-3-BCS according to the method of claim 1.

3. A process as claimed in claim 1 wherein the racemising agent is an organic acid or mineral acid.

4. A process as claimed in claim 3 wherein the racemising agent is selected from trifluoroacetic acid, acetic acid and hydrochloric acid.

5. A process as claimed in claim 1 wherein the racemising agent is (−)-3-BCS.

6. A process as claimed in claim 1 wherein the resolution of racemic N-benzyl-3-(4-fluorophenyl)-1,4-oxazin-2-one with (−)-3-BCS is effected in an organic solvent.

7. A process as claimed in claim 6 wherein the organic solvent is isopropyl acetate or ethyl acetate.

8. A process as claimed in claim 1 wherein the liberation of the chiral oxazinone free base from the (−)-3-BCS salt is effected using an aqueous base.

9. A process as claimed in claim 8 wherein the aqueous base is selected from 0.88 ammonia solution or an alkali metal carbonate or hydroxide.

10. A process as claimed in claim 1 wherein the the reaction mixture containing the N-benzyl-3-(S)-(4-fluorophenyl)-1,4-oxazin-2-one (−)-3-BCS salt prepared in step (i) is aged at reduced temperature for at least 1 hour prior to collection of the (−)-3-BCS salt.

11. The compound N-benzyl-3-(S)-(4-fluorophenyl)-1,4-oxazin-2-one in the form of its 3-bromocamphor-8-sulphonic acid salt.

* * * * *